United States Patent [19]
Carey

[11] Patent Number: 6,075,141
[45] Date of Patent: Jun. 13, 2000

[54] N$^\alpha$-α, α-DIMETHYL-3,5-DIALKOXYBENZYLCARBONYL AMINO ACID 3,4-DIHYDRO-3-HYDROXY-4-OXO-1,2,3-BENZOTRIAZIN-3-YL AND PENTAFLUOROPHENYL ESTERS

[75] Inventor: Robert I. Carey, Augusta, Ga.

[73] Assignee: University of Georgia Research Foundation, Inc., Athens, Ga.

[21] Appl. No.: 08/891,134

[22] Filed: Jul. 10, 1997

Related U.S. Application Data

[60] Provisional application No. 60/021,254, Jul. 10, 1996.

[51] Int. Cl.$^7$ .............................. C07K 1/00; C07D 251/00
[52] U.S. Cl. .......................... 544/180; 544/183; 530/333; 530/334; 530/335; 530/337; 530/338; 564/161; 564/170; 560/19
[58] Field of Search ..................................... 544/183, 180; 514/293; 560/19; 530/333–335, 337, 338; 564/161, 170

[56] References Cited

U.S. PATENT DOCUMENTS 4,093,610   6/1978   Abraham et al. ..................... 260/112.5

OTHER PUBLICATIONS

Atherton, E., et al. 1988 "Peptide synthesis. Part 10. Use of pentaflurophenyl esters of fluorenylmethoxycarboxyl amino acids in solid phase peptide synthesis" *Tetrahedron* 44:843–857.

Atherton, E., and Sheppard, R.C. (1985) "Solid phase peptide synthesis using N$_a$–Fluorenylmethoxycarbonylamino acid pentafluorophenyl esters" *J. Chem. Soc. Chem. Commun.* pp. 165–166.

Aterton, E., et al. (1988) "Peptide synthesis. Part 12. 3,4–Dihydro–4oxo–1, 2,3–benzotriazin–3–yl esters of fluoroenylmethoxycarbonyl amino acids as self–indicating reagents for solid phase peptide synthesis" *J. Chem. Soc. Perkin Trans. 1*:2887–2894.

Barany, G., Kneib–Cordonier, N., and Mullen, D.G. (1987) "Solid–phase peptide synthesis: a silver anniversary report" *Int. J. Pept. Protein Res.* 30:705–739.

Ben Ishai, D., and Berger, A. (1952) "Cleavage of N–carbobenzoxy groups by dry hydrogen bromide and hydrogen chloride" *J. Org. Chem.* 17:1564–1570.

Bergmann, M. and Zervas, L. (1935) "The synthesis of peptides of l–Lysine and their behavior with papain" *J. Biol. Chem.* 111:245–260.

Bergmann, M., and Zervas, L. (1932) "Über ein allgemeines verfahren der peptid–synthese" *Ber. dtsch Chem. Ges.* 65:1192–1201.

Birr, C., et al. (1972) "Der α,α–Dimethyl–3,5–dimethoxybenzyloxycarbonyl (Ddz)–Rest, eine photo–und säurelabile Stickstoff–S-chutzgruppe für die Peptidchemie" *Leibigs Ann. Chem.* 763:162–172.

Birr, C. (1975) In: *Peptides*, "The α,α–Dimethyl–3.5–dimethoxy–benzyloxycarbonyl (Ddz) protecting group in nonclassical peptide synthesis quantitative control and continuous recording in the merrifield synthesis" (Y. Wolman, Ed.,) pp. 117–122, John Wiley & Sons, New York.

Birr, C. (1978) (Monograph) *Reactivity and Structure, Concepts in Organic Chemistry 8* "Aspects of the Merrifield Peptide Synthesis." Springer–Verlag, Berlin–Heidelberg, New York.

Birr, C., et al. (1973) "Automatic merrifield synthesis of antamanide in a new reactor using a modified resin, and extremely acid– and photo– labile protecting group, and symmetrical t–butyloxy–carbonylamino acid anhydrides" In: *Peptides*, (H. Nesvadba, Ed.) 175–184. North Holland Publ. Comp., Amsterdam.

Birr, C., et al. (1979) "Synthesis of Thymosin α$_1$, a polypeptide of the thymus" *Agnew. Chem. Int. Ed. Engl.* 18(5):394–395.

Birr, C., et al. (1979) "Synthese von Thymosin α$_1$, einem polypeptid des thymus" *Angew. Chem.* 91:422–423.

Birr, C., et al. (1976) "Quantitative monitoring of the redox condensation of Ddz–amino acids in the merrifield synthesis of secretin sequences" In: *Peptides, Chemistry, Structure, Biology* (R. Walter and J. Meienhofer, Eds.) 409–417, Ann Arbor Sci. Publ., Ann Arbor.

Birr, C., (1977) "Total synthesis on gel phase of the mast–cell degranulating peptide by fragment condensation" In: *Peptides Proc. 5th Amer. Pept. Symp. (M Goodman and J Meienhofer, Eds.)*510–513, Wiley & Sons, New York.

Birr, C., and Pipkorn, R. (1979) "Total synthesis on the gel phase of insulin a chain by fragment condensation and its selective disulphide bridging to form insulin" In: *Peptides 1978* (I.Z. Siemion and G. Kupryszewski, Eds.) 625–629, Wroclaw University Press, Wroclaw.

Birr, C., et al. (1980) "Fully active semisynthetic insulin by selective formation of the disulphide bridges as an intermediate result of the total synthesis by fragment condensation on polymer phase" In: *Insulin, Chemistry, Structure and Function of Insulin and Related Hormones* (D. Brandenburg, et al. eds.) 51–58, W. De Gruyter, Berlin.

Birr, C., et al. (1979) "Preparative merits of the mixed anhydride (MA) method in the excess use of Ddz–amino acids in the peptide synthesis of biologically active new antamanide analogues" *Int. J. Peptide Protein Res.* 13:287–295.

(List continued on next page.)

*Primary Examiner*—Bennett Celsa
*Attorney, Agent, or Firm*—Greenlee, Winner & Sullivan, P.C.

[57] ABSTRACT

This invention provides Ddz-amino acid pentafluorophenyl esters and Ddz-amino acid 3,4-dihydro-3-hydroxy-4-oxo-1,2,3-benzotriazine (ODhbt) esters and their side-chain protected derivatives. Preferred esters and derivatives are crystalline solids. The invention also provides (α,α-Dimethyl-3,5-dimethoxybenzyl)-p-methoxycarbonylphenylcarbonate, an improved reagent for the introduction of the Ddz group. Pfp and ODhbt esters of this invention have favorable coupling to racemization ratios and are particularly suited for automated solid-phase peptide synthesis. The invention relates in addition to methods of making the esters of this invention and to methods of using these esters in peptide synthesis.

31 Claims, No Drawings

OTHER PUBLICATIONS

Birr, C., et al., (1985) "Chemical synthesis and immunoregulatory activity of twin–$\alpha_1$ the head–to–head dimer of thymosin–$\alpha_1$," In: *Peptide Chemistry 1985* (Y. Kiso, Ed.) 39–44, Protein Research Foundation, Osaka.

Birr, C., et al. (1981) "Synthesis of a new neuropeptide, the head activator from hydra" *FEBS Letters.* 131(2):317–321.

Birr, C., and Wengert–Muller, M. (1979) "Synthesis of the Mast cell degranulating (MCD) peptide from bee venom" *Angew. Chem. Int. Ed. Engl.* 18(2):147–148.

Birr, C., et al. "Recycling of Excess Peptides from Fragment Condensations with Carbonyldiimidazole/1–Hydrobenzotriazole Activation." *Proc. 17th Europ. Pept. Symp., Prague; Peptides, 1982*, (K. Blaha, Ed.), W. de Gruyter, Berlin, pp. 145–148.

Birr, C. and Schmitt, B. "The biomimetic gel phase synthesis of the RNA–Polymerase II inhibitor peptide 6–deshydroxy–amanullin" *Proc. 17th Europ. Pept. Symp., Prague; Peptides, 1982*, (K. Blaha, Ed.), W. de Gruyter, Berlin, pp. 227–232.

Bodanszky, M. and Williams, N.J. (1967) "Synthesis of secretin. I. The protected tetradecapeptide corresponding to sequence 14–27" *J. Am. Chem. Soc.* 89:685–689.

Carey, R.I., et al. (1996) "Protection of asparagine and glutamine during $N^x$–Bpoc–based solid–phase peptide synthesis" *Int. J. Pept. Protein Res.* 47:209–213.

Carpino, L.A. (1957) "Oxidative reactions of hydrazines. IV. Elimination of nitrogen from 1, 1–Disubstituted–2–arenesulfonhydrazides$^{1-4}$" *J. Am. Chem. Soc.* 79:4427–5749.

Carpino, L.A., and Han, G.Y. (1970) "The 9–fluorenylmethoxycarbonyl function, a new base–sensitive amino–protecting group" *J. Am. Chem. Soc.* 92:5748.

Ciaredelli, T.L., et al. (1982) "Activity of synthetic thymosin $\alpha_1$ C–terminal peptides in the azathioprine e–rosette inhibition assay" *Biochemistry.* 21:4233–4237.

Fields, G.B., and Noble, R.L. (1990) "Solid phase peptide synthesis utilizing 9–fluorenylmethoxycarbonyl amino acids" *Int. J. Pept. Protein Res.* 35:161–214.

Fischer, E. (1906) "Untersuchungen über aminosäuren, polypeptide and proteine" *Ber. dtsch Chem. Ges.* 39:530–611.

Galpin, I.J., et al. (1981) "Peptides–XXXXVI. Studies in the synthesis of an analogue of hen egg white lysozyme" *Tetrahedron* 37(17):3043–3050.

Galpin, I.J., et al. (1979) "Peptides–XXXVI. Synthesis of the 27–37 fragment of a lysozyme analogue" *Tetrahedron* 35:2785–2790.

Galpin, I.J., et al. (1981) "Peptides XXXXV. Synthesis of the 118–129 fragment of a lysozyme analogue" *Tetrahedron* 37(17):3037–3041.

Hudson, D. (1990) "Methodological implications of simultaneous solid–phase peptide synthesis: a comparison of active esters" *Peptide Res.* 3:51–55.

Hudson, D. (1988) "Methodological implications of simultaneous solid–phase peptide synthesis. 1. Comparison of different coupling procedures" *J. Org. Chem.* 53:617–624.

Kamber, B., et al. (1976) "Synthese von humaninsulin. III. Aufbau des geschützten zweikettigen fragments A(14–21)–B(17–30)" *Helv. Chim. Acta.* 59:2830–2840.

Kemp, D.S. (1981) "The amine capture strategy for peptide bond formation—an outline of progress" *Biopolymers* 20:1793–1804.

Kemp, D.S., and Carey, R.I. (1993) "Synthesis of a 39–peptide and a 25–peptide by thiol capture ligations: Observation of a 40–fold rate acceleration of the intramolecular O, N–Acyl–Transfer reaction between peptide fragments bearing only cysteine protective groups" *J. Org. Chem.* 58:2216–2222.

Kemp, D.S., and Carey, R.I. (1991) "Resolution of the histidine problem for thiol capture–synthesis of a 39 peptide" *Tetrahedron Lett.* 32:2845–2848.

Kemp, D.S., et al. (1988) "Practical preparation and deblocking conditions for N–x–(2(p–biphenylyl)–2–propyloxycarbonyl)–amino acid (N–$\alpha$–Bpoc–Xxx–OH) derivatives" *Int. J. Peptide Protein Res.* 31:359–372.

Kisfaluldy, L. and Schon, I. (1983) "Preparation and applications of pentafluorophenyl esters of 9–fluorenylmethyloxycarbonyl amino acids for peptide synthesis" *Synthesis* 325.

Kovacs, J., et al. (1970) "Rates of racemization and coupling of cystein active ester derivatives" *Chem. Comm.* 53–54.

Kovacs, J., et al. (1970) "Racemization of amino acid derivatives. Rate of racemization and peptide bond formation of cysteine active esters" *J. Org. Chem.* 35:1810–1812.

Merrifield, R.B. (1963) "The synthesis of a tetrapeptide" *J. Am. Chem. Soc.* 85:2149–2154.

Mojsov, S., and Merrifield, R.B. (1981) "Solid–phase synthesis of crystalline glucagon" *Biochemistry* 20:2950–2957.

Mukaiyama, T., et al. (1968) "A new method for peptide synthesis by oxidation–reduction condensation" *J. Amer. Chem. Soc.* 90(16):4490–4491.

Pipkorn, R., et al. (1983) "Carbonyldiimidazole/1–hydroxybenzotriazole activation in polymer phase synthesis of the arginine rich proalbumin hexapeptide extension" *Int. J. Peptide Protein Res.* 21:100–106.

Ramachandran, J., and Li, C.H. (1962) "Preparation of crystalline $N^G$–Tosylarginine derivatives" *J. Org. Chem.* 27:4006–4009.

Schmitt, B., and Birr, C. (1980) "Promoted dimerization of $\alpha$–methylstyrene by 3, 5–dimethoxy–substituents" *Chem. Letters Jap.* pp. 1005–1008.

Schwertner, E., et al. (1975) "Synthese einiger [2–(p–Biphenylyl)isopropylox–carbonyl]–aminosäurederivate" *Liebigs Ann. Chem.*, pp. 581–585.

Schwyzer, R. and Sieber, P. (1963) "Total synthesis of adrenocorticotrophic hormone" *Nature.* 199:172–174.

Sieber, P., et al. (1977) "Totalsynthese von humaninsulin. IV. Beschreibung der Endstufen" *Helv. Chim. Acta.* 60:27–37.

Sieber, P., and Iselin, B. (1968) "Peptidsynthesen unter verwundung der 2–(p–Diphenyl)–isopropyloxycarbonyl (Bpoc)–Aminoschutzgruppe" *Helv. Chim. Acta.* 51:614.

Sifferd, R.H., and du Vigneaud, V. (1935) "A new synthesis of carnosine, with some observations on the splitting of the benzyl group from carbobenzoxy derivatives and from benzylthio ethers" *J. Biol. Chem.* 108:753–761.

Veber, D.F., et al. (1968) "The synthesis of peptides in aqueous medium. IV. A novel protecting group for cysteine" *Tetrahedron Lett.* (26):3057–3058.

Wieland, Th., et al. (1978) "L,L–3,6–[Methanothio(2,3–indolo)methano] piperazin–2,5–dion, das kleinste phallotoxin–modellpeptid" *Angew. Chem.* 90:67–68.

Wieland, Th., et al. (1978) "L,L–3,6[Methanothio(2,3–indolo) methano] piperazine–2,5–dione, the smallest phallotoxin model" *Angew. Chem. Int. Ed. Engl.* 17:54–55.

Zanotti, G., et al. (1978) "Synthesis of monocyclic and bicyclic peptides of tryptathionine and glycine" *Int. J. Peptide Protein Res.* 12:204–216.

Zanotti, G., et al. (1989) "Structure–toxicity relationships in the amatoxin series" *Int. J. Peptide Res.* 34:222–228.

N^α-α, α-DIMETHYL-3,5-DIALKOXYBENZYLCARBONYL AMINO ACID 3,4-DIHYDRO-3-HYDROXY-4-OXO-1,2,3-BENZOTRIAZIN-3-YL AND PENTAFLUOROPHENYL ESTERS

This application claims priority under 35 USC 119(e) to application 60/021,254 filed Jul. 10, 1996.

FIELD OF THE INVENTION

This invention relates to $N^\alpha$-Ddz-amino acid compounds (Ddz=α,α-dimethyl-3,5-dimethoxy-benzylcarbonyl), namely Ddz-amino acid pentafluorophenyl (Pfp) esters and Ddz-amino acid 3,4-dihydro-4-oxo-1,2,3-benzotriazin-3-yl (ODhbt) esters, their preparation and their use in peptide, polypeptide and protein synthesis.

BACKGROUND OF THE INVENTION

The Ddz group was introduced by Birr in 1972[6] as an $N^\alpha$-urethane protecting group labile to dilute solutions of TFA in $CH_2Cl_2$. The use of this group allowed a milder overall procedure for the synthesis of peptides in the solid phase, compared to Boc-based strategies.[1-2] The Ddz group is cleaved within 15 minutes on the solid phase in 1–5% TFA (V/V) in $CH_2Cl_2$. With smaller peptides, 1% TFA in $CH_2Cl_2$ is adequate for quantitative removal of the Ddz group. With longer peptides, 5% TFA in $CH_2Cl_2$ is required, due to the larger number of amide bonds relative to the $N^\alpha$-Ddz group. Amide bonds are able to form hydrogen bonds with the reagent acid, effectively reducing its concentration to a point where cleavage is incomplete.

Birr and coworkers have demonstrated the applicability of Ddz-amino acids to solution and solid-phase peptide synthesis by synthesizing peptide fragments on the solid phase for subsequent fragment condensation in solution. In this manner, the mast-cell-degranulating peptide was synthesized both as the fully-protected peptide[35] and the free peptide.[36] Ddz-amino acids were also used to construct a protected insulin A-chain,[40-41] which upon deprotection was combined with natural B-chain from Bovine insulin to yield fully active semisynthetic insulin. Thymosin $\alpha_1$,[43-45] a 28-amino acid peptide, was synthesized completely in solution from fragment condensations.

Of particular note is the application of Ddz-amino acids to large scale solution-phase synthesis of five fragments of thymosin $\alpha_1$ and twin $\alpha_1$ peptides in amounts of 400 g or more.[45] In this synthesis, DCC/HOBt mediated couplings were used for the preparation of small peptide fragments that were then condensed using the azide method.

Zanotti and colleagues[48] applied Ddz-amino acids throughout their synthesis of amaninamides, analogs of the highly toxic mushroom amatoxins. Use of Boc-amino acids was not feasible, due to the presence of the acid-labile cysteine(S-trityl) residue, and use of Fmoc-amino acids was prohibited due to the protection of the C-terminal γ-hydroxyamino acid as the lactone, this functionality being sensitive to ring opening by amines. Hence, Birr has established coupling and deprotection for the employment of $N^\alpha$-Ddz amino acids in both solution and solid phase peptide synthesis.

In previous work,[6] most of the Ddz-amino acids were prepared as their corresponding dicyclohexylamine salts. These salts must be manually liberated and combined with an appropriate acylating agent prior to use in solid phase peptide synthesis.

Active esters (hydroxysuccinimide, nitrophenyl, 2,3,5-trichlorophenyl, or pentachlorophenyl)[15-16, 19-20, 49-50] of the acid-labile Bpoc-group have been synthesized, but were shown to be too inefficient for application to solid-phase synthesis. The Pfp and ODhbt esters of $N^\alpha$-Fmoc amino acids have also been prepared.

Kovacs noted the favorable properties of Pfp esters in his study of $N^\alpha$-urethane-protected cysteine derivatives,[50] in which Pfp esters were identified as having the highest $k_{coup}/k_{rac}$ ratio out of a wide range of active esters. Fmoc amino acid Pfp esters were first prepared in Kisfaludy[51] and were later applied to solid phase synthesis in an Fmoc/polyamide continuous flow system by Atherton and Sheppard.[52] Hudson,[53] in a comparison of couplings of active esters, stated that Pfp esters were the most suitable for routine use in SPPS, as they are usually crystalline, are prepared in high yield, and are stable to long periods of storage.

ODhbt esters have generally higher reactivity compared to OPpf esters, though their stability is said to be marginal. The in situ preparation of 3,4-dihydro-4-oxo-1,2,3-benzotriazin-3-yl (ODhbt) esters of certain urethane protected amino acids was disclosed by König and Geiger (43), but did not gain favor due to the formation of an o-azidobenzoic acid ester as a by-product of their preparation. Fmoc amino acid ODhbt esters, however, have been prepared as crystalline solids in acceptable yields by Atherton, et al,[54] and their use was demonstrated through the synthesis of the acyl carrier protein decapeptide sequence 65–74 and a nonadecapeptide sequence.

A recent review of solid-phase peptide synthesis is provided in Barany, G. et al.[2] This reference is specifically incorporated by reference in its entirety herein to provide details of solid-phase synthetic methods.

The present work relates to Pfp and ODhbt activated esters of $N^\alpha$-Ddz amino acids, particularly those that are crystalline, which have apparently not been reported previously.

SUMMARY OF THE INVENTION

An object of this invention is to provide active amino acid ester reagents for solution and solid-phase peptide synthesis. Preferred reagents must be sufficiently reactive to be practical for use in automated synthesis methods. Preferred reagents must also have a reasonably long shelf-life to be practical for commercial applications. Reagents that are crystalline solid materials are preferred for stability. Preferred reagents should also be resistant to racemization and their use should generate minimal undesirable side-products or by-products that would interfere with peptide synthesis. Preferred reagents and methods of synthesis using them should also be complimentary to existing technology and instrumentation for automated peptide synthesis.

More specifically, this invention provides Ddz-Xxx-Pfp and Ddz-Xxx-ODhbt amino acid esters (where Xxx represents any derivitized or non-derivitized amino acid), particularly those esters of amino acids, including side-chain protected amino acids, commonly employed in solution and solid-phase peptide synthesis. Preferred side-chain protecting groups are those that are removed under reaction conditions distinct from those used to remove the Ddz group itself. More preferred for solid-phase synthesis are side-chain protecting groups that are removed under reaction conditions distinct both from those used to remove the Ddz group and also distinct from those used to remove the synthesized peptide chain from the solid resin employed.

Another object of this invention is to provide procedures for the preparation of substantially pure, preferably crystalline, stable Ddz-Xxx-OPpf and Ddz-Xxx-ODhbt esters of amino acids.

This invention also extends to improved methods of solution and solid-phase peptide synthesis using the Ddz-Xxx-OPpf and Ddz-Xxx-ODhbt esters of this invention.

$N^\alpha$-Ddz amino acid Pfp esters and $N^\alpha$-Ddz amino acid ODhbt esters are stable, storable, solid materials, many of which are crystalline and, therefore, facilitate and simplify both solid and solution phase peptide synthesis, especially in automated peptide synthesizers, by eliminating the need for activations, filtrations, and couplings prior to the peptide bond forming reaction. The purification of peptides prepared in solution is greatly facilitated by the use of these compounds because of the substantial lack of by-products produced by coupling agents.

$N^\alpha$-Ddz amino acid Pfp, esters and $N^\alpha$-Ddz amino acid ODhbt esters can be used in combination with resin linkages (e.g. oxime, phenyl ester, thioester, allyl ester, p-hydroxybenzyl ester and PAL linkers, that are not stable to the repetitive basic reagents (typically 20% piperidine in DMF) used to remove $N^\alpha$-Fmoc groups.

$N^\alpha$-Ddz amino acid Pfp esters and $N^\alpha$-Ddz amino acid ODhbt esters can be used in combination with side-chain protecting groups and resin-linkages that are removable with trifluoroacetic acid/scavenger mixtures, distinguishing them from $N^\alpha$-Boc amino acid derivatives that require side-chain protecting groups and resin-linkages that are removable only with stronger acid (e.g., HF or trifluoromethanesulfonic acid)/scavenger mixtures.

$N^\alpha$-Ddz amino acid Pfp esters and $N^\alpha$-Ddz amino acid ODhbt active esters greatly facilitate peptide synthesis with $N^\alpha$-Ddz amino acids in comparison to the use of non-activated, storage stable salts for peptide couplings.

$N^\alpha$-Ddz amino acid Pfp esters and $N^\alpha$-Ddz amino acid ODhbt esters greatly facilitate peptide synthesis with $N^\alpha$-Ddz amino acids in comparison to the use of other $N^\alpha$-Ddz amino acid active esters (e.g. hydroxysuccinimide, pentachlorophenyl, 2,3,5-trichlorophenyl, or p-nitrophenyl) whose reactivity is too sluggish to be useful in practical application to solid-phase peptide synthesis.

This invention provides amino acid Pfp esters and amino acid ODhbt esters of the general formula:

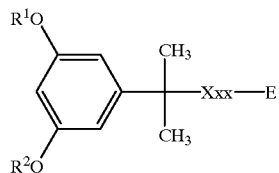

where B represents the ester moieties:

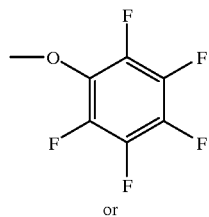

or

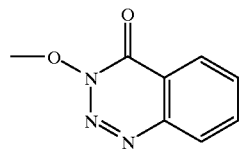

Xxx represents an amino acid, including a side group-protected amino acid, and $R^1$ and $R^2$ are small alkyl groups having from one to six carbon atoms.

Activated, N-protected amino acids of this invention can have the structures:

Formula I

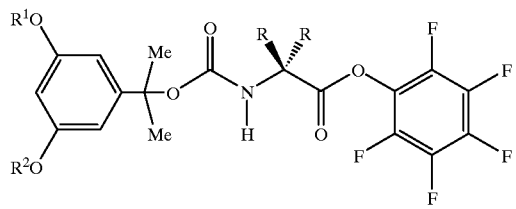

Formula II

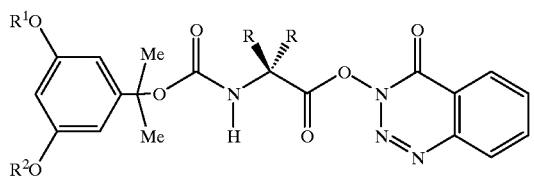

where R and R' most generally are any of the side groups of amino acids commonly used in peptide synthesis, including protected side groups commonly employed in peptide synthesis and $R^1$ and $R^2$, independently of one another are small alkyl groups having 6 or fewer carbon atoms. More specifically, R and R' are selected from hydrogen, alkyl, cycloalkyl, substituted alkyl, substituted cycloalkyl, aryl, or substituted aryl. $R^1$ and $R^2$ are preferably methyl or ethyl groups and more preferably are methyl groups. Substitution on alkyl cycloakyl and aryl groups includes substitution with halogens and other non-carbon atoms, including heterocyclic alkyl and aryl groups. Substitution includes, in particular, the substituents found in the amino acids that are naturally occuring, including those found in peptides.

This invention includes those esters of formula I and II in which one of R or R' is H and the other is the side chain on the α-carbon atom of an amino acid such as glycine, alanine, valine, leucine, isoleucine, proline, arginine, lysine, histidine, serine, threonine, aspartic acid, glutamic acid, asparagine, glutamine, cysteine, cystine, methionine, ornithine, norleucine, phenylalanine, tyrosine, tryptophan, β-alanine, homoserine, homoarginine, isoglutamine, pyroglutamic acid, γ-aminobutryic acid, citrulline, sarcosine, statine and the like, including derivatives with appropriate side group protection.

Storage stable Ddz esters of this invention include: Ddz-Gly-Pfp, Ddz-Val-Pfp, Ddz-Leu-Pfp, Ddz-Ile-Pfp, Ddz-Met-Pfp, Ddz-Phe-Pfp, Ddz-Tyr(allyl)Pfp, Ddz-Glu(tBu)-Pfp, Ddz-Asn(Trt)-Pfp, Ddz-Asp(tBu)-Pfp, Ddz-Gln(Trt)-Pfp, Ddz-Lys(Tfa)-Pfp, Ddz-Cys(tButhio)-Pfp, Ddz-Gly-OI)hbt, Ddz-Ala-ODhbt, Ddz-Val-ODhbt, Ddz-Ile-ODhbt, Ddz-Pro-ODhbt, Ddz-Trp-ODhbt, Ddz-Asn(Trt)-ODhbt, Ddz-Gln(Trt)-ODhbt, Ddz-Thr(tBu)-ODhbt, and Ddz-Ser-ODhbt.

The R and R' side chains of the amino acid may be protected as required, using common techniques and protecting groups well known to one skilled in the art, such as the commonly employed amino, hydroxy, thiol and carboxy protecting groups. Preferred side-chain protecting groups are those that are removed under conditions distinct from that of the Bpoc group. More preferred side-chain protecting groups for the compounds of this invention are t-butyl type and benzyl-type groups. For use herein, a t-butyl-type protective group includes those protective groups with similar deprotection chemistry as a t-butyl group, i.e., those protective groups that will be removed in approximately the same time as a t-butyl group, in acidolytic deprotection mixture. Similarly, for use herein, a benzyl-type group includes those protective groups that will be removed in approximately the same time as a benzyl group, in acidolytic deprotection mixture.

The compounds of this invention also include those of formula I and II in which both R and R' are side chains attached to the α-carbon of an amino acid as, for example, in the case of isovaline where one of R or R' is ethyl and the other is methyl.

The compounds of the invention also include esters of formula I and II wherein carbon atoms from the R or R' groups are part of a cyclic ring such as ortho-amino benzoic acid or 1-amino-2-carboxy cyclohexane.

As indicated in formulas I and II and as appreciated in the art, amino acids may be optically active. In most cases, L-amino acids (the form occurring in proteins) will be used in polypeptide synthesis. The activated N-protected amino acids of this invention can, however, be optically active in either the L- or D-form, including mixtures of enantiomers in which one form is in excess, or racemic mixtures of enantiomers.

The esters of this invention include among others Ddz-protected: Pfp and ODhbt esters of: Gly, Ala, Val, Leu, Ile, Pro, Met, Phe, Trp, Tyr(Allyl), Lys(Alloc), Asp(tBu), Glu(tBu), Ser(tBu), Thr(tBu), Asn(Trt), Gln(Trt), His(Trt), and Arg(Pmc).

This invention also provides method for preparing the Ddz amino acid reagents of this invention. In particular, α,α-dimethyl-3,5-dimethoxybenzyl-p-methoxycarbonylphenyl-carbonate, an improved reagent for the introduction of the Ddz group is provided.

The invention also includes the improvement in the synthesis of a polypeptide chain wherein an N-protected amino acid component is deprotected and the deprotected amino acid component is allowed to react with a second similar or dissimilar activated N-protected amino acid component and the process repeated until the desired polypeptide is obtained, said improvement comprising using as the activated N-protected amino acid component in at least one of said reactions a compound having the structure of Formula I or II where $R^1$, $R^2$, R and R' are defined above.

Yet another aspect of the invention involves an improvement in the solid phase synthesis of a polypeptide chain on an insoluble solid support wherein an N-protected amino acid component is coupled by condensation reaction to an insoluble solid support containing substituent groups reactive with the carboxyl terminus end of said amino acid component, the coupled N-protected amino acid component is deprotected, a second similar acid component in at least one of said reactions a compound or dissimilar activated N-protected amino acid component is coupled to said deprotected amino acid compound, and the process repeated until the desired polypeptide is obtained, said improvement comprising using as the activated N-protected amino having the structure for formula I or II, wherein $R^1$, $R^2$, R and R' are defined above. Preferred solid-phase methods of this invention are those in which the conditions for removal of the Ddz groups, side-chain protecting groups and for cleavage of the resin linkage are substantially orthogonal, i.e., substantially distinct.

DETAILED DESCRIPTION OF THE INVENTION

Synthesis. The synthesis of Ddz-Xxx-OH was first reported by Birr,[6] Pro, Cysteine, and Trp being prepared as the free acids, while Gly, Ala, Val, Ile, Phe, Tyr(OBzl), Cys(StBu), and Ser(tBu) were prepared and characterized as their dicyclohexylamine salts. As shown in Scheme 1, Ddz-Xxx-OH can be prepared from either Ddz-phenyl carbonate (Ddz-O-Ph), Ddz-p-methoxycarbonylphenyl carbonate (Ddz reagent), or Ddz-Azide. Some of the tert-butyl and trityl protected derivatives require a more reactive acylating such as Ddz-Azide. The free acid is immediately esterified in an appropriate solvent (EtOAc, THF, or Dioxane) to form the active ester.

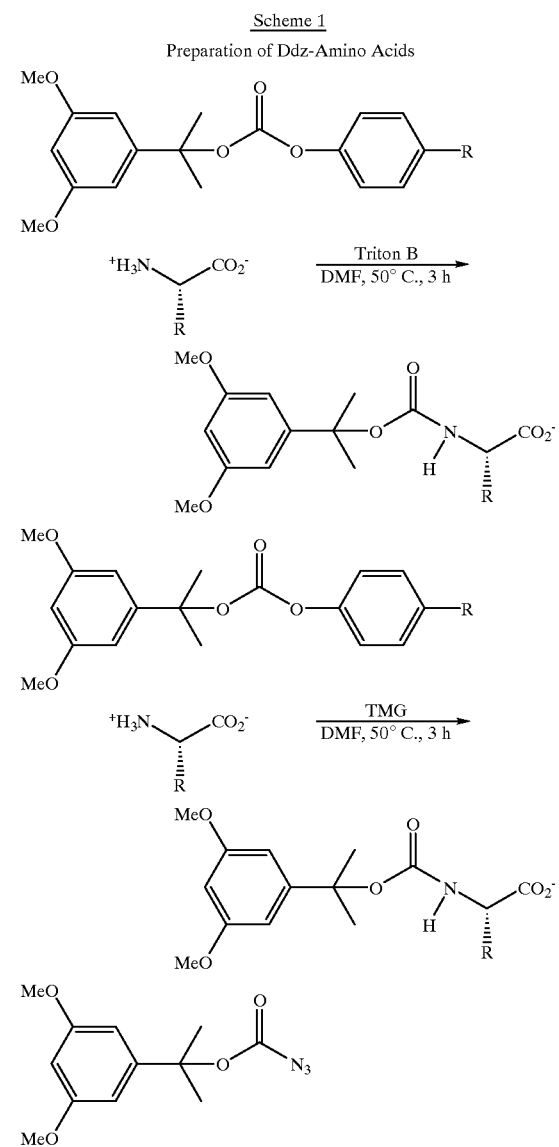

Scheme 1
Preparation of Ddz-Amino Acids

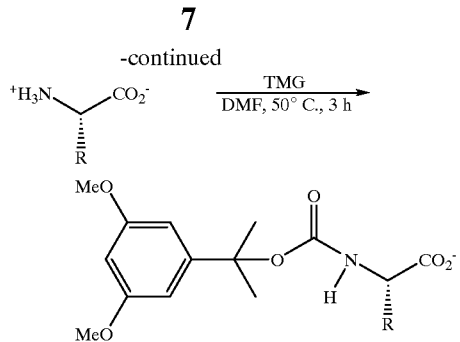

The Pfp esters of Ddz aliphatic amino acids: Gly, Val, Leu, Ile, Phe, and Met were crystalline solids, while Ala, Pro, and Trp esters were oils or foams. In addition, the Pfp ester of many trifunctional amino acids, including: Asn(Trt), Gln (Trt), Asp(tBu), Glu(tBu), Lys(Tfa), Tyr(OAllyl), Cys(St (tBUthio)Bu), and Arg(Pcm) were also obtained as crystalline solids. The more hydrophobic derivatives, Lys(Alloc), Ser(tBu), and Thr(tBu) gave oils as the Pfp esters, resisting all attempts at crystallization.

The inability to crystallize some of the above-mentioned derivatives led to the preparation of corresponding 3,4-dihydro-4-oxo-1,2,3-benzotriazine-3-yl (ODhbt) esters. The Ddz-Xxx-ODhbt esters of Ala, Pro, and Trp were easily prepared as crystalline solids, followed by Gly, Val, and Ile. In addition, the ODhbt esters of Ser and Thr were crystallized upon preparation, whereas Leu, Met, Phe, Cys(Stbu), Asp(tBu), and Glu(tBu) were obtained as foams. Ddz-Arg-(Pmc)Dhbt was isolated in about 92% purity including 5–6% of the γ-lactam impurity. Ddz-Arg(Pmc)Pfp was also isolated, but with somewhat less γ-lactam impurity. Examples of derivatives prepared are summarized in Table 1 and the examples.

TABLE 1

| Compound | Mol Wt. | mp (° C.) | $[\alpha]_D^{21\ 1}$ | HPLC[2] |
| --- | --- | --- | --- | --- |
| Ddz-Gly-Pfp | 467.37 | 92–95 | — | 10.24 |
| Ddz-Ala-Pfp | 477.40 | oil | −35.6 | 11.34 |
| Ddz-Val-Pfp | 505.45 | 79–80 | −39.3 | 14.56 |
| Ddz-Leu-Pfp | 519.48 | 82.5–83.5 | −35.8 | 15.58 |
| Ddz-Ile-Pfp | 519.48 | 66–68 | −30.7 | 15.85 |
| Ddz-Pro-Pfp | 503.43 | oil | −23.3 | 14.65 |
| Ddz-Met-Pfp | 524.49 | 105–106 | −25.4 | 13.41 |
| Ddz-Cys(StButhio)-Pfp | 597.62 | 65–75 | −70.0 | 17.31 |
| Ddz-Phe-Pfp | 553.49 | 130–132 | −12.5 | 15.12 |
| Ddz-Tyr(OAllyl)-Pfp | 609.56 | 94–96 | −12.4 | 16.50 |
| Ddz-Trp-Pfp | 592.53 | foam | −21.9 | 13.20 |
| Ddz-Ser(tBu)-Pfp | 549.50 | oil | −16.8 | 16.29 |
| Ddz-Thr(tBu)-Pfp | 563.53 | oil | −23.5 | 17.48 |
| Ddz-Asp(tBu)-Pfp | 577.51 | 88–90 | −24.6 | 15.00 |
| Ddz-Glu(tBu)-Pfp | 591.54 | 83–85 | −25.4 | 15.80 |
| Ddz-Asn(Trt)-Pfp | 762.74 | 133–136 | −15.3 | 18.23 |
| Ddz-Gln(Trt)-Pfp | 776.77 | 157–158 | −15.5 | 18.80 |
| Ddz-His(Trt)-OH | 607.64 | 176–178 | +27.8 | 5.42 |
| Ddz-Lys(Tfa)-Pfp | 630.50 | 109–110 | −18.9 | 11.82 |
| Ddz-Val-ODhbt | 484.50 | 109–112 | −104.2 | 12.24 |
| Ddz-Leu-ODhbt | 498.54 | foam | −93.5 | 15.2 |
| Ddz-Ile-ODhbt | 498.54 | 95–100 | −95.2 | 14.3 |
| Ddz-Pro-ODhbt | 482.49 | 112–116 | −81.4 | 11.12 |
| Ddz-Met-ODhbt | 516.57 | foam | −69.5 | 10.63 |
| Ddz-Cys(StButhio)-ODhbt | 576.68 | foam | −101.39 | 16.88 |
| Ddz-Phe-ODhbt | 532.56 | foam | −60.2 | 14.93 |
| Ddz-Tyr(OAllyl)-ODhbt | 588.62 | foam | −37.69 | 14.80 |
| Ddz-Trp-ODhbt | 571.60 | 110–112 d. | −49.1 | 13.84 |
| Ddz-Ser(tBu)-ODhbt | 528.60 | 133–136 | −36.6 | 14.40 |
| Ddz-Thr(tBu)-ODhbt | 542.59 | 71–73 | −22.4 | 15.68 |
| Ddz-Asp(tBu)-ODhbt | 556.50 | foam | −65.2 | 13.36 |
| Ddz-Glu(tBu)-ODhbt | 570.60 | foam | −77.07 | 13.65 |
| Ddz-Asn(Trt)-ODhbt | 741.80 | 111–116 | −46.4 | 16.8 |
| Ddz-Gln(Trt)-ODhbt | 755.83 | amorph. | −43.3 | 17.40 |
| Ddz-Lys(Tfa)-ODhbt | 609.86 | foam | −67.8 | 10.60 |
| Ddz-Ala-ODhbt | — | 127–131 | −124.2 | 9.74 |
| Ddz-Gly-ODhbt | — | 139–142 | — | 8.43 |

[1]All of the optical rotation values are reported for c = 1 in DMF. @ c = 0.5 in DMF.
[2]All HPLC values were obtained on a Vydac C18 HPLC column using an eluent 60% B to 100% B over twenty minutes. Eluent B = 0.1% TFA in 90% CH$_3$CN containing 10% water. Eluent A = 0.1% TFA in water.

The synthesis of N$^\alpha$-Ddz-Arg(Pmc)-Pfp and Ddz-Arg (Pmc)-ODhbt presented a special problem, as has been reported in conjunction with other N$^\alpha$-amino acid active esters.[54] Ddz-Arg(Pmc)-OH was prepared by reaction of H-Arg(Pmc)-OH with Ddz-Azide at 50° C. in DMF as shown in Scheme 1. The free acid was then immediately esterified in EtOAc or THF, and after removal of the DCU and concentration, a white solid was obtained from ether. Varying amounts of γ-lactam formation (5–15%) can be seen upon analysis of the product by HPLC and $^1$H-NMR. The $^1$H-NMR peaks are all broadened due to transformation to the lactam. The $^1$H-NMR shows complete lactam formation after 5 h in CDCl$_3$.

A variety of side-chain protecting groups can be employed with the Ddz esters of this invention. Among preferred side-chain protecting groups are those that are stable to repetitive treatments of 1% TFA in CH$_2$Cl$_2$, while being labile to 95% TFA scavenger cocktails. The use of tert-butyl esters and ethers in conjunction with N$^\alpha$-Ddz-amino acids has already been proven convincingly by Birr and coworkers. The incompatibility of the side-chain protected derivatives Lys(Boc) and Tyr(tBu) with these conditions has been mentioned elsewhere in relation to the Bpoc group, which may be cleaved in 0.5% TFA in CH$_2$Cl$_2$. In exemplary peptide syntheses described herein the side-chain protected derivatives Lys(Tfa) and Tyr(OAllyl) have been employed. The Tfa group here is cleaved under orthogonal conditions using a solution of piperidine in aqueous DMF or a solution of 0.1 M Ba(OH)$_2$ in 1:1 MeOH/H$_2$O.

In addition to tBu, TrE, tBu-thio, Pmc, Tfa, Bum and alloc and allyl side group-protecting group that are specifically exemplified in the examples herein, Dnp (dinitrophenyl), Mtr (methoxytrimethylbenzenesulfonyl), Adoc (adamantyloxycarbonyl), Tmse (trimethylsilylethyl) groups can be employed as is known in the art amino acid side group protecting groups. The choice of a particular protecting group depends, as is well understood in the art, upon the amino acid side group to be protected and upon the conditions (deprotection conditions, coupling conditions, etc.) that are to be used in a given polypeptide synthesis.

Compounds of this invention where R$^1$ and R$^2$ are alkyl groups other than methyl groups can be readily synthesized by those of ordinary skill in the art employing the methods described herein, or routine adaptation of those methods by routine choice of starting materials or reaction conditions.

Scheme 2 illustrates the synthesis of Ddz acetylating reagents that are provided herein for synthesis of Ddz esters. Details of this synthesis are provided in the Examples.

Solution Phase Couplings with Ddz-Xxx-Pfp and Ddz-Xxx-ODhbt. The efficiency of acylation of ODhbt esters, in terms of both coupling and racemization, was examined through the acylation of a simple amino acid alkyl ester, i.e., the acylation of H-Tyr-OMe with Ddz-L-Val-Dhbt and Ddz-D-Val-ODhbt in DMF at 0.1M. The dipeptides Ddz-L-Val-Tyr-OMe and Ddz-D-Val-Tyr-OMe were obtained in high yield (>90%) after a simple extractive workup and the Ddz-L-Val-Tyr-OMe gave a clean, single peak HPLC trace. Ddz-D-Val-ODhbt was not obtained as a solid, as it was contaminated with 5% of the azidobenzoate impurity, as mentioned by Atherton, et al.,[54] which showed up in the HPLC trace. Both dipeptides gave clean $^1$H-NMR spectra. The attempted separation of the diastereomeric dipeptides by HPLC was unsuccessful over a wide range of isocratic gradients. In the $^1$H-NMR spectra, however, there is a slight difference in shift of the Val α-CH between the two dipeptides, hence there is no evidence in either spectra of any measurable amount of racemization.

Solid Phase Synthesis with Ddz-Xxx-Pfp and Ddz-Xxx-ODhbt. A highly sterically hindered test sequence $^+$H$_3$N-Lys-Ile-Ile-Ile-Ile-Ile-NH$_2$, Met-Enkephalin, H-Tyr-Gly-Gly-Phe-Met-NH$_2$, and Neurokinin A, H-His-Lys-Thr-Asp-Ser-Phe-Val-Gly-Leu-Met-NH$_2$ were synthesized using the Ddz amino acid esters of this invention. All peptides were assembled on an MBHA$^1$ resin, using 4 equiv. of Ddz-Xxx-Pfp or Ddz-Xxx-ODhbt. The highly hindered sequence vias constructed with ODhbt esters since Pfp esters are reported to couple slowly in similar situations. The peptide was obtained in 50% yield upon cleavage from the resin with 1M Triflic acid/TFA/thioanisole and trituration (7×) with ether. ESI mass spectrometry confirmed the identity of the product.

the side-chain protection Ser(tBu), Asp(tBu), Thr(tBu), and His(Trt). The tert-butyl and trityl protecting groups were cleaved from the resin with neat TFA. Removal of the Tfa group from the resin-bound peptide was largely incomplete after overnight treatment with 3:1:1 DMF/H$_2$O/piperidine. However, quantitative removal of the Tfa group could be achieved by treatment of the cleaved peptide with 20% piperidine in 1:1 MeOH/H$_2$O. Alternately, the cleaved peptide could be treated with a solution of 0.1 M Ba(OH)$_2$ in 1:1 MeOH/H$_2$O. The crude peptide was recovered in 54% yield, giving a peak of 79% purity by HPLC. ESI mass spectrometry confirmed the identity of both Neurokinin A and the Lys(Tfa)-protected analog.

Pentafluorophenyl esters and 3,4-dihydro-4-oxo-1,2,3-benzotriazine-3-yl esters of the N$^\alpha$-Ddz-amino acid derivatives useful in solid phase synthesis can be prepared by the methods disclosed herein or by routine adaptation of those methods. Most of these esters, especially the Pfp esters, are well-behaved crystalline solids with shelf lives of well over a year when stored in parafilm sealed vials at −20° C. Application of these esters to several short syntheses demonstrates their usefulness in solution and solid-phase synthesis. These active esters require no further activation, although HOBt is normally added with the pentafluorophenyl esters to speed up the coupling rate to a point where it is comparable with that of symmetrical anhydrides. Thus, the active: ester protocol lends itself well to automation. The N$^\alpha$-Ddz-Xxx-Pfp and N$^\alpha$-Ddz-Xxx-ODhbt strategies are commercially viable methods for solid phase peptide synthesis.

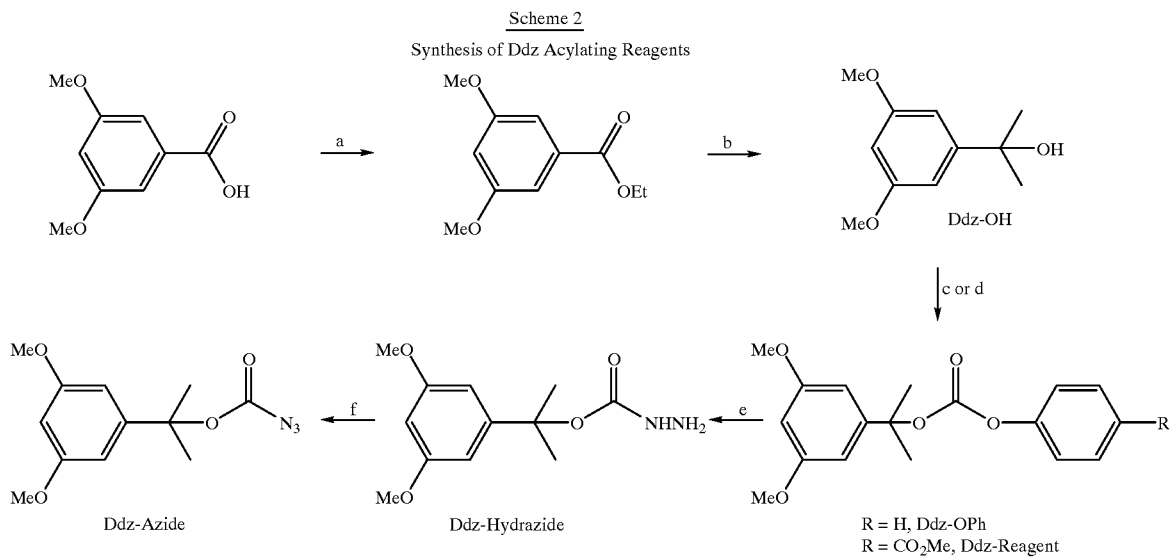

Scheme 2
Synthesis of Ddz Acylating Reagents

A mixture of Pfp and ODhbt esters was used in the synthesis of Met-Enkephalin, H-Tyr-Gly-Gly-Phe-Met-NH$_2$ and Neurokinin A, H-His-Lys-Thr-Asp-Ser-Phe-Val-Gly-Leu-Met-NH$_2$. For Met-Enkephalin, the side-chain protected Tyr(OAllyl) was used. The allyl group was removed on the resin by treatment with PdCl$_2$ and tri-n-butyltinhydride. The peptide was then cleaved with 1M Triflic acid/TFA/thioanisole to yield 63% of the expected product. HPLC showed a product of 52% purity, although an impurity of 31% corresponded to the allyl group still intact on the peptide, as shown by ESI mass spectrometry. Neurokinin A was synthesized using stepwise solid phase peptide synthesis on a methionine loaded MBHA resin, using While the Ddz-amino acid Pfp or ODhbt esters of the invention can be used in the synthesis of polypeptides by classical methods using a series of deprotection and coupling reactions, they are particularly well adapted for use in solid phase polypeptide synthesis. It should be understood that the, term "polypeptides" as used herein is meant to include peptides, glycopeptides, depsipeptides, peptidomimetic molecules, and proteins. Also, it should be understood that the present invention contemplates sequential peptide synthesis wherein N-protected amino acids other than Ddz-amino acid Pfp or ODhbt esters are employed as well as at least one Ddz-amino acid Pfp or ODhbt ester of the invention. In practice, however, the activated N-protected amino acid components used in each sequence are preferably the Ddz-amino acid Pfp or ODhbt esters of this invention.

In solid phase polypeptide synthesis, an insoluble solid support or matrix, advantageously in bead form, is used. Such solid supports can be any of the solid phase polymeric substrates conventionally employed for the synthesis of polypeptides. Typical of such polymeric resins are crosslinked polystyrene resins, glass beads, clays, Celite, crosslinked dextran, polyacrylamides, polyamide resins, polyethylene glycol grafted polystyrene, and similar insoluble solid supports which either naturally contain reactive sites for coupling with the amino acid components or which can be provided with such reactive sites.

If desired, the solid phase polypeptide synthesis of the invention can be carried out in a flow reactor under pressure as described in U.S. Pat. No. 4,192,798, incorporated by reference in its entirety herein, but the use of supratmospheric pressures is not essential.

Several preliminary operations are necessary before the solid phase synthesis of a peptide can be started. First the, supporting resin containing the C-terminal amino acid component of the proposed peptide chain must be prepared. This can be accomplished by any of a number of procedures known to one skilled in the art. Many of these solid supports, derivatized with N-protected amino acids, are articles of commerce and may be purchased as desired. Many of the common resin linkages (for the preparation of C-terminal peptide amides, peptide acids, and the like) can be prepared with Bpoc-amino acids as easily as with the other N-protected amino acids, and this may be accomplished by any of a number of procedures known to be skilled in the art.

The remaining synthesis to form the desired polypeptide sequence is carried out in the following manner. Before coupling of the second amino acid can take place, the first residue already on the support must be deprotected. Deprotection of the first amino acid residue on the resin as well as of each of the subsequently coupled amino acid residues can be carried out by contacting, the protected amino acid residue with an appropriate deprotecting agent. The deprotecting agents employed for this purpose are well known to those of ordinary skill in the art of peptide synthesis and the particular deprotecting agent employed in any given instance will depend, of course, upon the deprotecting group on the amino acid/resin. For example, if the protecting group is t-butyloxycarbonyl, trifluoroacetic acid (usually 50% or higher) in dichloromethane or hydrochloric acid in a suitable solvent such as dioxane may be used. On the other hand, if the protecting group is 9-fluorenylmethyloxycarbonyl, basic conditions such as piperidine (usually 20%) in DMF will be the preferred method. If the protecting group for the first amino acid attached to the resin is Bpoc, the deprotecting agent of choice will be 0.5% TFA in dichloromethane. If the protecting group for the first amino acid is a Ddz group then the preferred deprotection agent is 5% TFA in dichloromethane.

After the deprotecting step, the resin is washed with a suitable solvent in order to remove excess deprotecting agents. The resin-bound free amine, thus prepared, is now ready for coupling with the next N-protected amino acid.

If the next N-protected amino acid is a Ddz-amino acid Pfp or ODhbt ester of the invention, it need not be activated and can be reacted directly in the presence of a non-nucleophilic tertiary amine base with the support now containing an unprotected resin bound amino acid. If, however, the N-protected amino acid component is to be coupled by more conventional procedures, it will be necessary to first activate, that is, convert it into a reactive form by any of a number of accepted procedures known to those of ordinary skill in the art of peptide synthesis. In general, an excess of the activated N-protected amino acid component is employed in the reaction. Concentration of the activated N-protected amino acid component is usually 0.1 M or greater.

After the coupling of the, second protected amino acid component to the first amino acid component, the attached protected dipeptide is then deprotected, neutralized if necessary, and washed as described above before coupling of the next amino acid derivative is effected. This procedure is repeated until the desired sequence of amino acids has been assembled on the insoluble support. The completed peptide can be removed from the insoluble support by any of the standard methods as, for instance, by cleavage with trifluoroacetic acid (for appropriately functionalized alkoxybenzyl alcohol, alkoxybenzyl amine, or alkoxybenzhydrylamine resins), $Pd^0$/tributyltin hydride mixtures in dichloromethane (for appropriately functionalized allyl-type linkers), aminolysis, alcoholysis, or hydrolysis (for appropriately functionalized of the phenyl ester or oxime type).

After cleavage from the solid support, the resulting peptide is found to be remarkably homogenous and to require no or minimal purification. Because of the very low contamination of byproducts overall yields are found to be surprisingly high and whatever purification is necessary can be carried out with relative ease. Such purifications are preferably carried out by partition chromatography, ion exchange chromatography, reversed-phase high performance liquid chromatography or a combination of both. Such procedures are well-known to one skilled in the art of peptide synthesis.

The following examples illustrate the invention and are not intended to limit the scope of the invention.

EXAMPLES

Materials and Methods. All amino acids and amino acid derivatives were purchased from either Peptides International (U.S.A.) or Advanced Chemtech (U.S.A.) and used without further purification. All other chemicals were purchased from Aldrich. Mass spectra were obtained on a Sciex API-1 single quadrupole instrument in the electrospray ionization mode. Routine $^1H$ NMR spectra were obtained on Brucker AM-250 FT (250 MHz) or AM-300 FT (300 MHz) spectrometers. $^{13}C$ NMR spectra were obtained on the same instruments (62.9 and 75.5 MHz). Chemical shifts are reported in ppm downfield from tetramethylsilane. THF was distilled over sodium and benzophenone. Analytical HPLC was performed on a Vydac 218TP54 reversed-phase C-18 column and preparative HPLC was performed on a Vydac 218 TP1022 reversed-phase C-18 column. All gradients reported are linear using two buffers, Eluent A (0.1% TFA aq.) and Eluent B (0.1% TFA in 90% MeCN aq.).

Abbreviations used for amino acids and the designations of peptides follow the rules of the IUPAC-IUB Commission of Biochemical Nomenclature, see: *J. Biol. Chem.* (1972) 247, 977–983. Other abbreviations used are those generally known to those in the art including: Acm (acetamidomethyl); EtOAc (ethyl acetate); Boc (tert.-butyloxycarbonyl); tBu (tert.-Iutyl); DCC (N,N'-dicyclohexylcarbodiimide); DCU (N, N'-dicyclohexylurea); DIC (diisopropylcarbodiimide); DIEA (N,N-diisopropylethylamine); DMF (N,N-dimethylformamide); Fmoc (9-fluorenylmethyloxycarbonyl); TFA (trifluoroacetic acid); TFMSA (trifluormethanesulfonic acid); Tfa (trifluoroacetate); Trt (trityl); Pmc (pentamethylchroman); MBHA (4-methylbenzhydrylamine resin); MeCN (acetonitrile); as well as other abbreviations identified, for example, in Barany et al. (47).

Ethyl 3,5-Dimethoxylbenzoate. A 500-mL round bottom flask that was flame dried and swept with $N_2$ was fitted with a drying tube and pressure-equalizing addition funnel. To the flask was added 100% ethanol (270 mL) which was cooled to 0° C. in an ice bath. $SOCl_2$ (26.2 mL, 0.36 mol) was added to the ethanol with vigorous stirring over 15 minutes. This mixture was allowed to warm to room temperature, at which point 3,5-dimethoxybenzoic acid (59.6 g, 0.327 mol) was added to the flask. The reaction mixture was heated in an oil bath (45–50° C.) overnight. During this time the solution changed from a cream-colored suspension to an orange-brown solution. The solvent was removed at reduced pressure (40° C.) to yield a brown oil, which was taken up in ether (250 mL) and washed with ice-cold 10% $KHCO_3$ (4×), water (2×), dried over $Na_2SO_4$, and the solvent removed in vaciao to give an orange brown oil (67.1 g, 97.6%). The oil was purified by Kugelrohr distillation, a clear oil (63.4 g, 92.2%) being collected at 120° C./1.0 torr. TLC: Rf=0.72 in 3/1 hexanes/ethyl acetate.

2-(p-3,5-Dimethoxyphenylyl)-2-propanol, Ddz alcohol. To a 1 liter 3-necked flask (flame-dried, $N_2$) was added a 3.0 M solution of methylmagnesium bromide (136 mL, 480 mmol). While cooling to 0° C. in an ice bath, a solution of ethyl 3,5-dimethoxybenzoate (40 g, 190 mmol) in ether (190 mL) was added through a pressure-equalizing addition funnel over a period of one hour. The reaction was allowed to warm to room temperature and was stirred overnight (12–15 h). During this time the solution changed from a brown to cloudy grey. TLC: Rf=0.38 in 3/1 hexanes/EtOAc. The reaction mixture was cooled to 0° C. and cold water was slowly added until bubbling ceased. More water was then added to total 400 mL. The solution was then acidified to pH 4 with solid citric acid. The phases were separated and the aqueous phase extracted with ether (3×150 mL) then washed with 10% $KHCO_3$ (4×), water (4×), dried over $Na_2SO_4$, and the solvent removed at reduced pressure to yield a pale yellow oil. The product crystallized as white needles (33.6 g, 90.3%) after being placed under high vacuum. The product was recrystallized from benzene/hexanes to yield 30.3 g in the first crop and 1.2 g in the second crop. Overall yield: 31.5 g, 84.6%. mp 51–53° C. (lit. 55° C.).

4-methyloxycarbonylphenyl chloroformate. A 20% solution of phosgene (170 mL, 0.33 mol) in toluene was added to a 500 mL pear-shaped flask (flame-dried, $N_2$). To the flask was added methyl-p-hydroxybenzoate (42.6 g, 0.28 mol) with stirring. Through an addition funnel was added pyridine (26.7 mL, 0.33 mol) in toluene while the reaction mixture was cooled in an ice bath so that the temperature did not exceed 20° C. The solution turned a yellowish color during the addition. The reaction mixture was stirred for 3 h, at which point the mixture was filtered on a buchner funnel. The pyridinium salts were washed with toluene (150 mL) and the combined organic phase washed with 1 N HCl (2×), water (2×), dried over $CaCl_2$ and $Na_2SO_4$, and the toluene removed in vacuo to yield yellowish crystals. After continued drying, the product (38 g, 63%) turned a greyish color. m.p. 52–53° C. (lit. 51–52° C.).

($\alpha,\alpha$-Dimethyl-3,5-dimethoxybenzyl)-p-methoxycarbonylphenyl-carbonate. To a 250 mL flask (flame-dried, $N_2$) fitted with an addition funnel was added a solution of the above prepared Ddz-OH (5.0 g, 25.4 mmol) in $CH_2Cl_2$ (25 mL). While the solution was cooled to -5° C. in an ice/salt bath, dry pyridine (2.56 mL, 31.6 mmol) was added with stirring. To the stirred solution was added p-acetyl-phenyl chloroformate (6.0 g, 27.9 mmol) in $CH_2Cl_2$ (12–13 mL) over a period of 30 minutes. During the addition, the reaction mixture turned from clear yellow to a greyish suspension. The solution was allowed to stir overnight (15 h) at 0° C. The reaction mixture was then filtered into 50 mL ice-cold water and the precipitate washed with $CH_2Cl_2$ until colorless. The phases were separated and the organic phase washed with 1N HCl (2×), water (2×), dried over $Na_2SO_4$, and the solvent removed at reduced pressure to yield greyish crystals (7.7 g, 81.1%). The product was recrystallized from a benzene/hexanes mixture. mp 64–67° C.

($\alpha,\alpha$-Dimethyl-3,5-dimethoxybenzyl)-phenylcarbonate, Ddz-O-Ph. To a 250 mL flask (flame-dried, $N_2$) fitted with an addition funnel was added a solution of the above prepared Ddz-OH (25.5 g, 0.13 mmol) in $CH_2Cl_2$ (130 mL). While the solution was cooled to -5° C. in an ice/salt bath, dry pyridine (12.5 mL, 0.15 mmol) was added with stirring. To the stirred solution was added phenyl chloroformate (16.9 mL, 0.135 mmol) in $CH_2Cl_2$ (70 mL) over a period of 30 minutes. During the addition, the reaction mixture turned from a clear to bright yellow solution. The solution was allowed to stir overnight (15 h) at 0° C. during which time a white precipitate formed. The reaction mixture was filtered into 400 mL ice-cold water and the precipitate washed with $CH_2Cl_2$ (40–50 mL) until colorless. The phases were separated and the organic phase washed with water (5×), dried over $Na_2SO_4$, and the solvent was removed at reduced pressure to yield a pale yellow oil, which crystallized as a white solid (40.0 g, 98.0%) when left under high vacuum. The product was recrystallized from benzene/hexanes to yield long, white needles (31.1 g, 76.2%). mp 61.5–63° C.

2-(3,5-Dimethoxyphenylyl)-2-propyloxycarbonylhydrazide To a stirred solution of Ddz-O-Ph (10 g, 0.0316 mol) in DMF (15 mL) at 0° C. was added 64% Hydrazine (10.9 ml., 0.221 mol). The reaction mixture was stirred overnight at 0° C., then poured into 75 mL ice water and allowed to stir for 8 hours at 0° C. The white precipitate was collected, washed with cold 1N NaOH (40 mL), and washed with cold water until the washings were neutral. The yield upon drying under vacuum was 7.25 g, 90%. The solid was recrystallized from methanol. Yield: 6.3 g, 78%. mp 110–111° C., Lit: 108° C.

Ddz-azide. A suspension of the above prepared Ddz-Hydrazide (7.0 g, 0.027 mol) in acetonitrile (90 mL) was cooled to -25° C. in a dry ice-35% methanol-65% $H_2O$ bath. Upon cooling, a mixture of 6N HCl (15 mL) in acetonitrile (30 mL) was added to the solution in one portion. The cloudy suspension cleared upon addition of the acid. After cooling to -25° C. again, a 5M $NaNO_2$ solution (6.0 mL, 0.030 mol) was added over a period of 10 min, the temperature being kept below -15° C. After 10–15 min of stirring, the solution was neutralized to pH paper with 2N $Na_2CO_3$. A small amount of a white precipitate formed at this point. The solution was poured into cold $H_2O$ (350 mL), the aqueous layer extracted with ether (3×), and the combined ether layers washed with $H_2O$ (1×), dried over $Na_2SO_4$, and concentrated under high vacuum to yield a white solid (6.07 g, 84.8%). mp 68–73° C. (lit. 70° C.).

General Procedure for preparation of Ddz-Xxx-OH with Triton B. The free acid, Ddz-Xxx-OH, was prepared according to the procedure of Kemp et. al. (23) for Bpoc-Xxx-OH amino acids with the following modifications. The amino acid zwitterion (20 mmol) was solubilized in Triton B (22 mmol of a 40% solution in MeOH) and then concentrated on a high vacuum rotary evaporator to remove any excess $H_2O$ and $CH_3OH$. The white syrupy solid was mixed well with DMF (3–4 mL) and the suspension concentrated to a syrup on a high vacuum rotary evaporator. This step was repeated three times. The resulting heavy syrup was mixed with a minimum amount of DMF (5 mL) and Ddz-O-Ph (20 mmol), and placed in a 55° C. silicon oil bath. After stirring for 3 h, the DMF was removed with the high vacuum rotovap. The pasty solid was diluted with $H_2O$ (20 mL), $Na_2SO_4$ (0.5 g, helps to prevent emulsions in some cases), and then overlayered with ether (20 mL). The layers were separated and the aqueous phase extracted twice more with ether. The combined ether washes were back extracted with 5% $NaHCO_3$ aq. and the aqueous phases combined, cooled in a 0° C. ice bath and overlayered with ether (40 mL). Dropwise addition of 1.0 M pH 3.5 citrate buffer to the biphasic mixture caused clouding in the aqueous layer that was cleared upon swirling. Addition was continued until pH 3.5 was reached in the mixture. The aqueous phase was extracted with ether (3×25 ml,) and the ether combined and washed with citrate buffer (2×25 mL), water (2×25 ml,), brine (1×25 mL), dried over $MgSO_4$, filtered and concentrated in vacuo to an oily solid (Yields: 60–95%).

General Procedure for preparation of Ddz-Xxx-OH with tetramethylguanidine. To a solution of the amino acid zwitterion (20 mmol) and Ddz-azide (20 mmol) in DMF (10 mL) was added tetramethylguanidine (40 mmol). After stirring under $N_2$ for 4 h, the reaction was poured into cold 5% $NaHCO_3$ (40 mL) and extracted with ether (4×20 mL). The combined ether layers were back-extracted with 5% $NaHCO_3$ (1×10 mL). The combined aqueous layers were cooled to 4° C. in an ice bath, overlayered with EtOAc (25 mL), and acidified to pH 3.5 by addition of 1.0 M pH 3.5 citrate buffer. The acidic aqueous layer was extracted twice more with EtOAc (25 mL), and the EtOAc layers were combined and washed with citrate buffer (1×), water (2×), brine (1×), dried over $MgSO_4$, and concentrated in vicuo.

General Procedure for the Esterification with Pentafluorophenol. The Ddz-Xxx-OH (20 mmol) prepared above was dissolved in THF (20 mL) and cooled to OC in an ice bath. Pentafluorophenol (19.5 mmol) and DCC (20 mmol) were added sequentially in one portion and the reaction allowed to stir for 2 h. The reaction was then filtered to remove DCU, the THF removed in vacuo, and the reaction taken up in ether (10 mL) and allowed to sit overnight in a −20° C. freezer. Residual DCU was removed by filtration and the ether was removed in vacuo to an oil that either crystallized in isopropanol/hexanes or remained as an oil.

General Procedure for the Esterification with 3,4-Dihydro-3-Hydroxy-4-Oxo-1,2,3-Benzotriazineone, HODhbt. The Ddz-Xxx-OH (20 mmol) prepared above was dissolved in THF (20 mL) and cooled to −10° C. in an acetone ice bath. DCC (20 mmol) was added in one portion, and after stirring 5 min, HODhbt (19.5 mmol) was added and the reaction was allowed to stir at −10° C. for 30 min followed by stirring at 0° C. for 3 h. The reaction was then filtered to remove DCU, the THF removed in vacuo, and the reaction taken up in ether, if soluble, and allowed to sit overnight in a −20° C. freezer. Iesidual DCU was removed by filtration and the ether was removed in vacuo to an oil that either crystallized in EtOAc/hexanes, ether/hexanes, or remained as a foam upon removal of the ether and placement under high vacuum. For those derivatives insoluble in ether, the reaction was taken up in EtOAc and allowed to sit overnight in a −20° C. freezer. Sifter removal of residual DCU and EtOAc, the resulting oil was crystallized from EtOAc/hexanes or by addition of ether with the aid of a sonicator when necessary.

Ddz-Gly-ODhbt. General procedure w/Triton B used to prepare Ddz-Gly-OH. Esterification in THF, −10° C. Crystallization from THF/ether. Yield 23%. mp 5.139–142° C. HPLC (55% B to 100% B over 20 min.): $t_R$=8.43. Crystallization from ether. Yield 76.8%. mp 127–131° C. $[\alpha]^{21}589$=−124.2. HPLC (55% B to 100% B over 20 min.): $t_R$=9.74.

Ddz-Val-ODhbt. General procedure w/Triton B used to prepare Ddz-Val-OH. Esterification in THF, −10° C. Crystallization from ether/hexanes. Yield 76.0%. mp 109–112° C. $[\alpha]^{21}589$=−104.2. HPLC (55% B to 100% B over 20 min.): $t_R$=112.2

Ddz-Ile-ODhbt. General procedure w/Triton B used to prepare Ddz-Ile-OH. Esterification in THF, −10° C. Crystallization from EtOAc/hexanes. Yield 71.0%. mp 95–100° C. $[\alpha]^{21}589$=−95.2. HPLC (55% B to 100% B over 20 min.): $t_R$=14.3.

Ddz-Leu-ODhbt. General procedure w/Triton B used to prepare Ddz-Leu-OH. Esterification in THF, −10° C. Yield 54.4%. $[\alpha]^{21}589$=−93.5. HPLC (55% B to 100% B over 20 min.): $t_R$=15.2.

Ddz-Pro-ODhbt. General procedure w/Triton B used to prepare Ddz-Pro-OH. Esterification in dioxane, 5° C. Crystallization from ether/hexanes. Yield 50.0%. mp 112–116° C. $[\alpha]^{21}589$=−81.4. HPLC (55% B to 100% B over 20 min.): $t_R$=11.1.

Ddz-Asn(Trt)-ODhbt. General procedure w/tetramethylguanidine used to prepare Ddz-Asn(Trt)-OH. Esterification in THF, −10° C. Crystallization from ether. Yield 66.0%. mp 111–116° C. $[\alpha]^{21}589$=−46.4. HPLC (55% B to 100% B over 20 min.): $t_R$=16.8.

Ddz-Gln(Trt)-ODhbt. General procedure w/tetramethylguanidine used to prepare Ddz-Gln(Trt)-OH. Esterification in THF, −10° C. Crystallization from ether. Yield 81.4%. mp $[\alpha]^{21}589$=−43.28. HPLC (55% B to 100% B over 20 min.): $t_R$=17.4.

Ddz-Asp(tBu)-ODhbt. General procedure w/tetramethylguanidine used to prepare Ddz-Asp(tBu)-OH. Esterification in THF, −10° C. Yield 60.0%. $[\alpha]^{21}589$=−65.2. HPLC (55% B to 100% B over 20 min.): $t_R$=13.4.

Ddz-Glu(tBu)-ODhbt. General procedure w/tetramethylguanidine used to prepare Ddz-Glu(tBu)-OH. Esterification in THF, −10° C. Yield 58.1%. $[\alpha]^{21}589$=−77.1. HPLC (55% B to 100% B over 20 min.): $t_R$=13.6.

Ddz-Ser(tBu)-ODhbt. General procedure w/tetramethylguanidine used to prepare Ddz-Ser(tBu)-OH. Esterification in dioxane, 5° C. Crystallization from ether. Yield 57.0%. mp 133–136° C. $[\alpha]^{21}589$=−36.6. HPLC (55% B to 100% B over 20 min.): $t_R$=14.4.

Ddz-Thr(tBu)-ODhbt. General procedure w/tetramethylguanidine used to prepare Ddz-Thr(tBu)-OH. Esterification in THF, −10° C. Crystallization from ether/hexanes. Yield 65.0%. $[\alpha]^{21}589$=−22.4. HPLC (55% B to 100% B over 20 min.): $t_R$=15.7.

Ddz-Cys(tButhio)-ODhbt. General procedure w/tetramethylguanidine used to prepare Ddz-Cys(tButhio)-OH. Esterification in THF, −10° C. Yield 66.2%. $[\alpha]^{21}589$=−101.4 HPLC (55% B to 100% B over 20 min.): $t_R$=16.9.

Ddz-Met-ODhbt. General procedure w/Triton B used to prepare Ddz-Met-OH. Esterification in THF, −10° C. Yield 62.7%. $[\alpha]^{21}589$=−69.5. HPLC (55% B to 100% B over 20 min.): $t_R$=10.6.

Ddz-Tyr(Allyl)-ODhbt. General procedure w/tetramethylguanidine used to prepare Ddz-Tyr(Allyl)-OH. Esterification in THF, −10° C. Yield 73.0%. $[\alpha]^{21}589$=−37.7. HPLC (55% B to 100% B over 20 min.): $t_R$=14.8.

Ddz-Phe-ODhbt. General procedure w/Triton B used to prepare Ddz-Phe-OH. Esterification in THF, −10° C. Yield 65.4%. $[\alpha]^{21}589=-60.2$. HPLC (55% B to 100% B over 20 min.): $t_R=13.7$.

Ddz-Lys(Tfa)-ODhbt. General procedure w/tetramethylguanidine used to prepare Ddz-Lys(Tfa)-OH. Esterification in THF, -10° C. Yield 73.7%. $[\alpha]^{21}589=-67.8$. HPLC (55% B to 100% B over 20 min.): $t_R=10.6$.

Ddz-Trp-ODhbt. General procedure w/tetramethylguanidine used to prepare Ddz-Trp-OH. Esterification in THF, -10° C. Crystallization from EtOAc/ether. Yield 47.0%. mp 110–112° C. dec. $[\alpha]^{21}589=-49.1$. HPLC (55% B to 100% B over 20 min.): $t_R=13.8$.

Ddz-His(Trt)-OH. General procedure w/tetramethylguanidine used to prepare Ddz-His(Trt)-OH. Yield 60.0%. mp 176–178° C. $[\alpha]^{21}589=+27.8$. HPLC (55% B to 100% B over 20 min.): $t_R=5.42$.

Ddz-Gly-Pfp. General procedure w/Triton B used to prepare Ddz-Gly-OH. Esterification in THF, 0° C. Crystallization from isopropanol/hexanes. Yield 71.4%. mp 92–95° C. HPLC (60% B to 100% B over 20 min.): $t_R=10.24$.

Ddz-Ala-Pfp. General procedure w/Triton B used to prepare Ddz-Ala-OH. Esterification in THF, 0° C. Yield 76.9%. $[\alpha]^{21}589=-35.6$. HPLC (60% B to 100% B over 20 min.): $t_R=11.34$.

Ddz-Val-Pfp. General procedure w/Triton B used to prepare Ddz-Val-OH. Esterification in THF, 0° C. Crystallization from ethanol/water. Yield 38.6%. mp 79–80° C. $[\alpha]^{21}589=-39.3$. HPLC (60% B to 100% B over 20 min.): $t_R=14.6$.

Ddz-Ile-Pfp. General procedure w/Triton B used to prepare Ddz-Ile-OH. Esterification in THF, 0° C. Crystallization from isopropanol/hexanes. Yield 42.6%. mp 66–68° C. $[\alpha]^{21}589=-30.7$. HPLC (60% B to 100% B over 20 min.): $t_R=15.8$.

Ddz-Leu-Pfp. General procedure w/Triton B used to prepare Ddz-Leu-OH. Esterification in THF, 0° C. Crystallization from isopropanol/hexanes. Yield 48.8%. mp 82.5–83.5° C. $[\alpha]^{21}589=-35.8$. HPLC (60% B to 100% B over 20 min.): $t_R=15.58$.

Ddz-Pro-Pfp. General procedure w/Triton B used to prepare Ddz-Pro-OH. Esterification in THF, 0° C. Yield 93.0%. $[\alpha]^{21}589=-23.3$. HPLC (60% B to 100% B over 20 min.): $t_R=14.6$.

Ddz-Asn(Trt)-Pfp. General procedure w/tetramethylguanidine used to prepare Ddz-Asn(Trt)-OH. Esterification in THF, 0° C. Crystallization from isopropanol/hexanes. Yield 46.1%. mp 133–136° C. $[\alpha]^{21}589=-15.3$. HPLC (60% B to 100% B over 20 min.): $t_R=18.2$.

Ddz-Gln(Trt)-Pfp. General procedure w/tetramethylguanidine used to prepare Ddz-Gln(Trt)-OH. Esterificatior. in THF, 0° C. Crystallization from isopropanol/hexanes. Yield 59.8%. mp 157–158° C. $[\alpha]^{21}589=15.5$. HPLC (60% B to 100% B over 20 min.): $t_R=18.8$.

Ddz-Asp(tBu)-Pfp. General procedure w/tetramethylguanidine used to prepare Ddz-Asp(tBu)-OH. Esterification in THF, 0° C. Crystallization from Hexanes. Yield 70.6%. mp 88–90° C. $[\alpha]^{21}589=-24.6$. HPLC (60% B to 100% B over 20 min.): $t_R=15.0$.

Ddz-Glu(tBu)-Pfp. General procedure w/tetramethylguanidine used to prepare Ddz-Glu(tBu)-OH. Esterification in THF, 0° C. Crystallization from ether/hexanes. Yield 76.9%. mp 83–85° C. $[\alpha]^{21}589=-25.4$. HPLC (60% B to 100% B over 20 min.): $t_R=15.8$.

Ddz-Ser(tBu)-Pfp. General procedure w/tetramethylguanidine used to prepare Ddz-Ser(tBu)-OH. Esterification in THF, 0° C. Yield 51.6%. $[\alpha]^{21}589=-36.6$. HPLC (60% B to 100% B over 20 min.): $t_R=16.3$.

Ddz-Thr(tBu)-Pfp. General procedure w/tetramethylguanidine used to prepare Ddz-Thr(tBu)-OH. Esterification in THF, 0° C. Yield 75.0%. $[\alpha]^{21}589=-15.5$. HPLC (60% B to 100% B over 20 min.): $t_R=17.48$.

Ddz-Cys(tButhio)-Pfp. General procedure w/tetramethylguanidine used to prepare Ddz-Cys(tButhio)-OH. Esterification in THF, 0° C. mp 65–75° C. Yield 74.0%. $[\alpha]^{21}589=-70.0$. HPLC (60% B to 100% B over 20 min.): $t_R=17.3$.

Ddz-Met-Pfp. General procedure w/Triton B used to prepare Ddz-Met-OH. Esterification in THF, 0° C. Crystallization from isopropanol/hexanes. Yield 41.1%. mp 105–106° C. $[\alpha]^{21}589=-25.4$. HPLC (60% B to 100% B over 20 min.): $t_R=13.4$.

Ddz-Tyr(Allyl)-Pfp. General procedure w/tetramethylguanidine used to prepare Ddz-Tyr(Allyl)-OH. Esterification in THF, 0° C. Crystallization from isopropanol/hexanes. Yield 65.3%. $[\alpha]^{21}589=-12.4$. HPLC (60% B to 100% B over 20 min.): $t_R=16.5$.

Ddz-Phe-Pfp. General procedure w/Triton B used to prepare Ddz-Phe-OH. Esterification in THF, 0° C. Crystallization from isopropanol/hexanes. Yield 61.7%. mp 130–132° C. $[\alpha]^{21}589=-12.5$. HPLC (60% B to 100% B over 20 min.): $t_R=15.1$.

Ddz-Lys(Tfa)-Pfp. General procedure w/tetramethylguanidine used to prepare Ddz-Lys(Tfa)-OH. Esterification in THF, 0° C. Crystallization from isopropanol/hexanes. Yield 82.3%. mp 109–110° C. $[\alpha]^{21}589=-67.8$. HPLC (60% B to 100% B over 20 min.): $t_R=10.6$.

Ddz-Trp-Pfp. General procedure w/tetramethylguanidine used to prepare Ddz-Trp-OH. Esterification in THF, 0° C. Yield 53.4%. $[\alpha]^{21}589=-21.9$. HPLC (60% B to 100% B over 20 min.): $t_R=13.2$.

Those of ordinary skill in the art will appreciate that methods, techniques, procedures, syntheses, starting materials, side-chain protecting groups, reagents and reaction conditions other than those specifically described herein can be employed with expense of undue experimentation to achieve the objects of this invention. All such routine adaptation or modifications or functional equivalents of the specific embodiments and examples disclosed herein are considered to fall within the spirit and scope of this invention.

All references cited herein are incorporated in their entirety by reference herein.

REFERENCES

1. Barany, G., and Merrifield, R. B. (1979) The Peptides (E. Gross and J. Meienhofer, eds.) 2, pp. 1–284, Academic Press. New York.
2. Barany, G., Kneib-Cordonier, N., and Mullen, D. G. (1987) Int. J. Pept. Protein Res. 30, 705–739.
3. Carpino, L. A., and Han, G. Y. (1970) J. Am. Chem. Soc. 92, 5748.
4. Fields, G. B., and Noble, R. L. (1990) Int. J. Pept. Protein Res. 35, 161–214.
5. Sieber, P., and Iselin, B. (1968) Helv. Chim. Acta. 51, 614.
6. Birr, C., Lochinger, W.., Stahnke, G., and Lang, P. (1972) Liebigs Ann. Chem. 763, 172–172.
7. Fischer, E. (1906) Ber. dtsch Chem. Ges. 39, 530.
8. Bergman, M., and Zervas, L. (1932) Ber. dtsch Chem. Ges. 65, 1192.

9. Ben Ishai, D., and Berger, A. (1952) *J. Org. Chem.* 17, 1564.
10. Sifferd, R. H., and du Vigneaud, V. (1935) *J. Biol. Chem.* 108, 753–761.
11. Harington, C. R., and Mead, T. H. (1935) *J. Biochem.* 29, 1602–1611.
12. Vigneaud, V. du, Ressler, C., Swan, J. M., Roberts, C. W., Katsoyannis, P. G., and Gordon, S. (1953) 75, 4879–4880.
13. Schwyzer, R., and Sieber, P. (1963) *Nature* 199, 172–174.
14. Bodansky, M., and Williams, N. J. (1967) *J. Am. Chem. Soc.* 89, 685–689.
15. Galpin, I. J., Kenner, G. W., Ohlsen, S. R., Ramage, R., Sheppard, R. C., and Tyson, R. G., (1979) *Tetrahedron* 35, 2785–2790.
16. Galpin, I. J., Hancock, F. E., Handa, B. K., Jackson, A. G., Kenner, G. W., McDowell, P., Noble, P., and Ramage, R. (1981) *Tetrahedron,* 37, 3043–3050.
17. Merrifield, R. B. (1963) *J. Am. Chem. Soc.* 85, 2149–2154.
18. Carpino, L. A. (1957) *J. Am. Chem. Soc.* 79, 4427.
19. Kamber, B., Riniker, B., Sieber, P., and Rittel, W. (1976) *Helv. Chim. Acta.* 59, 2830–2840.
20. Sieber, P., Kamber, B., Hartmann, A., Joehl, A., Riniker, B., and Rittel, W. (1977) *Helv. Chim. Actaz.* 60, 27–37.
21. Mojsov, S., and Merrifield, R. B. (1981) *Biochemistry,* 20 2950–2957.
22. Kemp, D. S. (1981) *Biopolymers* 20, 1793–1804.
23. Kemp, D. S., and Carey, R. I. (1993) *J. Org. Chem.* 58, 2216–2222.
24. Kemp, D. S., and Carey, R. I. (1991) *Tetrahedron Lett.* 32, 2845–2848.
25. Schmitt, B., and Birr, C. (1980) *Chem. Letters Jap.,* 1005–1008.
26. Ramachandran, J., and Li, C. H. (1962) *J. Org. Chem.* 27, 4006.
27. Bergmann, M., and Zervas, L. (1935) *J. Biol. Chem.* 111, 245.
28. Carey, R. I., Huang, H., Wadsworth, J. L., and Burrell, C. S. (1996) *Int. J. Pept. Protein Res.* 47, 209–213.
29. Birr, C. (1975) In: Peplides, 1974 (Y. Wolman, Ed.,) pp 117–122, John Wiley & Sons, New York.
30. Birr, C. (1978) (Monograph) Reactivity and Structure, Concepts in Organic Chemistry, Vol 8: Aspects of the Merrifield Peptide Synthesis, Springer-Verlag, Berlin-Heidelberg-New York.
31. Veber, D. F., Milkowski, J. D., Denkewalter, R. G., and Hirschmann, R. (1968) *Tetrahedron Lett. pp.* 3057.
32. Birr, C., Flor, F., Fleckenstein, P., and Wieland, Th. (1973) In: Peptides 1971 (H. Nesvadba, Ed.) pp. 175–184, North Holland Publ. Comp., Amsterdam.
33. Birr, C., Ueki, M., and Frank, R. (1976) In: Peptides, Chemistry, Structure, Biology (R. Walter and J. Meienhofer, Eds.) pp. 409–417, Ann Arbor Sci. Publ., Ann Arbor.
34. Mukaiyama, T., Ueki, M., Maruyama, H., and Matsueda, R. (1968) *J. Amer. Chem. Soc.* 90, 4490.
35. Birr, C., Wengert-Müller, M., and Buku, A. (1977) In: Peptides Proc. 5th Amer. Pept. Symp. (M. Goodman and J. Meienhofer, Eds.) pp. 510–513, Wiley & Sons, New York.
36. Birr, C., and Wengert-Müller, M. (1979) *Angew. Chem. Int. Ed. Engl.* 18, 147–148.
37. Wieland, Th., Birr, C., and Zanotti, G. (1978) *Angew. Chemie* 90, 67–68; (1978) *Angew. Chem. Int. Ed. Engl.* 17, 54–55.
38. Zanotti, G., Birr, C., and Wieland, T. (1978) *Int. J. Peptide Protein Res.* 12, 204–216.
39. Birr, C., and Schmitt, B. (1983) *Proc. 17th Europ. Pept. Symp.,* 1982, Prague (K. Blaha, Ed.) pp. 227–232, W. de Gruyter, Berlin.
40. Birr, C., and Pipkorn, R. (1979) In: Peptides 1978 (I. Z. Siemion and G. Kupryszewski, Eds.) pp. 625–629, Wroclaw University Press, Wroclaw.
41. Birr, C., Pipkorn, R., Gattner, H-G., Renner, R., and H äring, H-U. (1980) In: Insulin, Chemistry, Structure and Function of Insulin and Related Hormones (D. Brandenburg, et al. eds.), pp. 51–58, W. De Gruyter, Berlin.
42. Birr, C., Nassal, M., and Pipkorn, R. (1979) *Int. J. Peptide Protein Res.* 13, 287–295.
43. Birr, C., and Stollenwerk, U. (1979) *Angew. Chem.* 91, 422–423; (1979) *Angew. Chem. Int. Ed. Engl.* 18, 394–395.
44. Ciaredelli, T. L., Incefy, G. S., and Birr, C. (1982) *Biochemistry* 21, 4233–4237.
45. Birr, C., Heinzel, W., Nebe, C. Th., Ho, A., Stehle, B. (1986) In: Peptide Chemistry 1985 (Y. Kiso, Ed.), pp. 39–44, Protein Research Foundation, Osaka.
46. Birr, C., Zachmann, B., Bodenmuller, H., and Schaller, H. C. (1981) *FEBS Letters,* 131, 317–321.
47. Pipkorn, R., Schmid, M., Weigand, K., and Birr, C. (1983) *Int. J. Peptide Protein Res.* 21, 100–106.
48. Zanotti, G., Wieland, T., Benedetti, E., Di Blasio, B., Pavone, V., and Pedone, C. (1989) *Int. J. Peptidle Protein Res.* 34, 222–228.
49. Schwertner, E., Berndt, H., Gielen, H-G., and Zahn, H. (1975) *Liebigs Ann. Chem.,* 581–585.
50. Kovacs, J., Mayers, G. L., Johnson, R. H., Cover, R. E., and Ghatak, U. R. (1970) *Chem. Comm.,* 53–54; and Kovacs, J., Mayers, G. L., Johnson, R. H., Cover, R. E., and Ghatak, U. R. (1970) *J. Org. Chem.* 35, 1810–1812.
51. Kisfaluldy, L., and Schon, I. (1983) *Synthesis* 325.
52. Atherton, E., Carmeron, L. R., and Sheppard, R. C. *Tetrahedron* 44, 843–857;
Atherton, E., and Sheppard, R. C. (1985) *J. Chem. Soc. Chem. Comm.* 165–166.
53. Hudson, D. (1990) *Peptide Res.* 3, 51–55; and Hudson, D. (1988) *J. Org. Chem.* 53, 617–624.
54. Atherton, E., Holder, J. L., Meldal, M., Sheppard, R. C., and Valerio, R. M. (1988) *J. Chem. Soc. Perkin Trans.* 1, 2887–2894.
55. Kemp, D. S., Fotouhi, N., Boyd, J. G., Carey, R. I., Ashton, C., and Hoare, J. (1988) *Int. J. Peptide Protein Res.* 31, 359–372.

I claim:

1. An $N^\alpha$-protected activated amino acid ester represented by the formula:

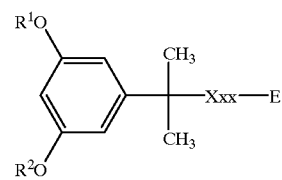

where Xxx represents an amino acid residue;
$R^1$ and $R^2$, independently of one another, are small alkyl groups having from one to six carbon atoms and
E is a pentafluorophenyl group or a 3,4-dihydro-3-hydroxy-4-oxo-1,2,3-benzotriazin-3-yl group.

2. The amino acid ester of claim 1 wherein Xxx represents a side-group protected amino acid residue.

3. The amino acid ester of claim 1 wherein $R^1$ and $R^2$ are methyl or ethyl groups.

4. The amino acid ester of claim 1 wherein Xxx represents an amino acid residue or side-group protected amino acid residue of glycine, alanine, valine, leucine, isoleucine, proline, arginine, lysine, histidine, serine, threonine, aspartic acid, glutamic acid, asparagine, glutamine, cysteine, cystine, methionine, ornithine, norleucine, phenylalanine, tyrosine, tryptophan, β-alanine or homoserine.

5. The amino acid ester of claim 1 wherein E is a pentafluorophenyl group.

6. The amino acid ester of claim 5 wherein $R^1$ and $R^2$ are methyl or ethyl groups.

7. The amino acid ester of claim 6 wherein $R^1$ and $R^2$ are methyl groups.

8. The amino acid ester of claim 7 wherein Xxx represents an amino acid residue or side group protected amino acid residue of an amino acid selected from the group consisting of glycine, alanine, valine, leucine, isoleucine, proline, arginine, lysine, histidine, serine, threonine, aspartic acid, glutamic acid, asparagine glutamine, cysteine, cystine, methionine, ornithine, norleucine, phenylalanine, tyrosine, tryptophan, β-alanine and homoserine.

9. The amino acid ester of claim 7 wherein Xxx represents an amino acid selected from the group consisting of glycine, alanine, valine, leucine, isoleucine, proline, methionine, phenylalanine and tryptophan.

10. The amino acid ester of claim 7 wherein Xxx represents a side group protected amino acid residue of an amino acid selected from the group consisting of aspartic acid, glutamic acid, asparagine, glutamine, serine, threonine, cysteine, tyrosine, arginine, histidine and lysine.

11. The amino acid ester of claim 1 which is Ddz-Gly-Pfp; Ddz-Ala-Pfp; Ddz-Val-Pfp; Ddz-Ile-Pfp; Ddz-Leu-Pfp; Ddz-Pro-Pfp; Ddz-Met-Pfp; Ddz-Phe-Pfp; Ddz-Trp-Pfp; Ddz-Asn-(Trt)-Pfp; Ddz-Gln(Trt)-Pfp; Ddz-Asp(tBu)-Pfp; Ddz-Glu(tBu)-Pfp; Ddz-Ser(tBu)-Pfp; Ddz-Thr(tBu)-Pfp; Ddz-Cys(tButhio)-Pfp, Ddz-Try(Allyl)-Pfp; Ddz-Lys(Tfa)-Pfp, Ddz-Arg(PMC)-Pfp; or Ddz-His(Trt)-Pfp.

12. The amino acid ester of claim 1 which is Ddz-Gly-Pfp; Ddz-Val-Pfp; Ddz-Leu-Pfp; Ddz-Ile-Pfp; Ddz-Asn(Trt)-Pfp; Ddz-Gln(Trt)-Pfp; Ddz-Asp(tBu)-Pfp; Ddz-Glu(tBu)-Pfp; Ddz-Cys(tButhio)-Pfp; Ddz-Met-Pfp; Ddz-Tyr(Allyl)-Pfp; Ddz-Phe-Pfp; or Ddz-Lys(Tfa)-Pfp.

13. The amino acid ester of claim 1 which is a 3,4-dihydro-4-oxo-1,2,3-benzotriazin-3-yl ester.

14. The amino acid ester of claim 13 wherein $R_1$ and $R_2$ are methyl or ethyl groups.

15. The amino acid ester of claim 13 wherein $R_1$ and $R_2$ are methyl groups.

16. The amino acid ester of claim 15 wherein Xxx represents an amino acid residue or side group protected amino acid residue of an amino acid selected from the group consisting of glycine, alanine, valine, leucine, isoleucine, proline, arginine, lysine, histidine, serine, threonine, aspartic acid, glutamic acid, asparagine glutamine, cysteine, cystine, methionine, ornuihine, norleucine, phenylalanine, tyrosine, tryptophan, β-alanine and homoserine.

17. The amino acid ester of claim 15 wherein Xxx represents an amino acid selected from the group consisting of glycine, alanine, valine, leucine, isoleucine, proline, methionine, phenylalanine and tryptophan.

18. The amino acid ester of claim 15 wherein Xxx represents a side group protected amino acid residue of an amino acid selected from the group consisting of aspartic acid, glutamic acid, asparagine, glutamine, serine, threonine, cysteine, tyrosine, arginine, histidine and lysine.

19. The amino acid ester of claim 15 which is Ddz-Gly-ODhbt; Ddz-Ala-ODhbt; Ddz-Val-ODhbt; Ddz-Ile-ODhbt; Ddz-Leu-ODhbt; Ddz-Pro-ODhbt; Ddz-Met-ODhbt; Ddz-Phe-ODhbt; Ddz-Trp-ODhbt; Ddz-Asn(Trt)-ODhbt; Ddz-Gln(Trt)-ODhbt; Ddz-Asp(tBu)-ODhbt; Ddz-Glu(tBu)-ODhbt; Ddz-Ser(tBu)-ODhbt; Ddz-Thr(tBu)-ODhbt; Ddz-Cys(tButhio)-ODhbt; Ddz-Try(Allyl)-ODhbt; Ddz-Lys-(Tfa)-ODhbt; Ddz-Arg(PMC)-ODhbt; or Ddz-His(Trt)-ODhbt.

20. The amino acid ester of claim 15 which is Ddz-Gly-ODhbt; Ddz-Val-ODhbt, Ddz-Ala-ODhbt; Ddz-Ile-ODhbt, Ddz-Pro-ODhbt; Ddz-Asn(Trt)-ODhbt; Ddz-Gln(Trt)-ODhbt; Ddz-Ser(tBu)-ODhbt; Ddz-Thr(tBu)-ODhbt; Ddz-Arg(PMC)-ODhbt; or Ddz-His(Trt)-ODhbt.

21. A compound of formula:

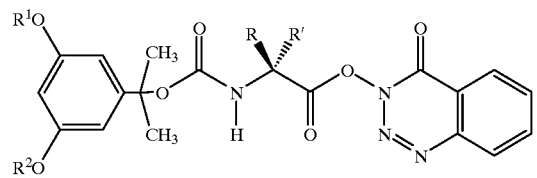

wherein $R^1$ and $R^2$ independently of one another, are alkyl groups having from one to six carbon atoms; and R and R' are selected from the group consisting of hydrogen, alkyl groups, cycloalkyl groups, aryl groups, alkyl groups substituted with halogens and other non-carbon atoms, cycloalkyl groups substituted with halogens and other non-carbon atoms, and aryl groups substituted with halogens and other non-carbon atoms.

22. The compound of claim 21 where $R^1$ and $R^2$ are methyl or ethyl groups.

23. The compound of claim 21 wherein $R^1$ and $R^2$ are methyl groups.

24. A compound of formula

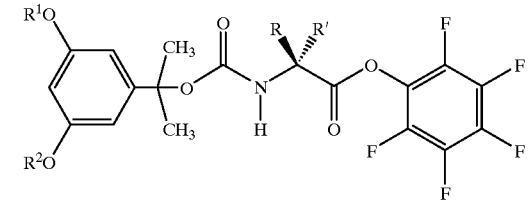

wherein $R^1$ and $R^2$, independently of one another, can be alkyl groups having from one to six carbon atoms and R and R', independently of one another, can be hydrogen, alkyl groups, cycloalkyl groups, aryl groups, alkyl groups substituted with halogens and other non-carbon atoms, cycloalkyl groups substituted with halogens and other non-carbon atoms, or aryl groups substituted with halogens and other non-carbon atoms.

25. The compound of claim 24 wherein $R^1$ and $R^2$ are ethyl or methyl groups.

26. The compound of claim 24 wherein $R^1$ and $R^2$ are methyl groups.

27. In a method for synthesizing a polypeptide comprising the steps of deprotecting an N-protected amino acid component and reacting said deprotected amino acid component with an N-protected activated amino acid ester, the improvement wherein an amino acid ester of claim 1 is employed as said N-protected activated amino acid ester.

28. The method of claim 27 wherein in said amino acid ester $R^1$ and $R^2$ are methyl groups.

29. The method of claim 27 wherein the synthesis is performed on an insoluble solid support.

30. The method of claim 29 wherein said N-protected amino acid component is N-protected with an α,α-dimethyl-3,5-dimethoxybenzylcarbonyl group.

31. The method of claim 29 wherein said N-protected amino acid activated ester is deprotected employing a 1–5% TFA solution in $CH_2Cl$ as the deprotecting agent.

* * * * *

UNITED STATES PATENT AND TRADEMARK OFFICE
CERTIFICATE OF CORRECTION

Page 1 of 2

PATENT NO. : 6,075,141

DATED : June 13, 2000

INVENTOR(S) : R.I. Carey

It is certified that error appears in the above-identified patent and that said Letters Patent is hereby corrected as shown below:

In column 3, line 56, delete "B" and replace with --E--.

In column 8, line 45, delete "TrE" and replace with --Trt--.

In column 10, line 26, delete the colon which follows "active".

In column 10, line 60, delete the comma which follows "the".

In column 13, line 18, delete "vaciao" and replace with --vacuo--.

In column 15, line 34, delete "vicuo" and replace with --vacuo--.

In column 15, line 37, delete "OC" and replace with --0°C--.

In column 15, line 56, delete "Iesidual" and replace with --Residual--.

In column 15, line 62, delete "Sifter" and replace with --After--.

In column 16, line 10, delete "112.2" and replace with --12.2--.

In column 19, line 26, delete "*Actaz.*" and replace with --*Acta*--.

In column 20, line 28, delete "*Peptidle*" and replace with --*Peptide*--.

UNITED STATES PATENT AND TRADEMARK OFFICE
CERTIFICATE OF CORRECTION

Page 2 of 2

PATENT NO. : 6,075,141
DATED : June 13, 2000
INVENTOR(S) : R. I. Carey

It is certified that error appears in the above-identified patent and that said Letters Patent is hereby corrected as shown below:

In column 21, line 57, delete "ornuihine" and replace with --ornithine--.

Signed and Sealed this

Twenty-second Day of May, 2001

*Attest:*

NICHOLAS P. GODICI

*Attesting Officer*  Acting Director of the United States Patent and Trademark Office